US006822114B1

(12) United States Patent \
Williams et al.

(10) Patent No.: US 6,822,114 B1 \
(45) Date of Patent: Nov. 23, 2004

(54) PROCESS FOR PRODUCTION OF FLUOROALKOXY-SUBSTITUTED BENZAMIDES AND THEIR INTERMEDIATES

(75) Inventors: Eric L. Williams, Zachary, LA (US); Tse-Chong Wu, Baton Rouge, LA (US)

(73) Assignee: Albemarle Corporation, Richmond, VA (US)

( * ) Notice: Subject to any disclaimer, the term of this patent is extended or adjusted under 35 U.S.C. 154(b) by 107 days.

(21) Appl. No.: 10/266,959

(22) Filed: Oct. 8, 2002

(51) Int. Cl.$^7$ ............................................. C07L 65/00
(52) U.S. Cl. ....................... 562/474; 562/848; 562/840; 568/630; 568/631
(58) Field of Search ................................ 562/474, 848, 562/840; 568/630, 631

(56) References Cited

U.S. PATENT DOCUMENTS

| | | |
|---|---|---|
| 3,496,184 A | 2/1970 | Mizzoni et al. |
| 3,544,568 A | 12/1970 | Cragoe, Jr. et al. |
| 3,761,592 A | 9/1973 | Mizzoni et al. |
| 4,634,713 A | 1/1987 | Werner et al. |
| 5,376,656 A | 12/1994 | Amschler |
| 5,712,298 A | 1/1998 | Amschler |
| 6,174,878 B1 | 1/2001 | Gamache et al. |
| 6,331,543 B1 | 12/2001 | Garvey et al. |
| 6,436,970 B1 | 8/2002 | Hafner et al. |

FOREIGN PATENT DOCUMENTS

| | | |
|---|---|---|
| EP | 0 109 606 A1 | 5/1984 |
| JP | 58069812 | 4/1983 |
| JP | 62158253 | 7/1987 |
| WO | WO 92/12961 | 8/1992 |
| WO | WO 00/53182 | 9/2000 |
| WO | WO 00/66123 | 11/2000 |
| WO | WO 01/13953 A2 | 3/2001 |
| WO | WO 01/15677 A2 | 3/2001 |
| WO | WO 01/15678 A2 | 3/2001 |
| WO | WO 01/32165 A1 | 5/2001 |
| WO | WO 01/60358 A1 | 8/2001 |

OTHER PUBLICATIONS

Chem Abs. 134: 240172 JP 2001085055 Mar. 30, 2001.*
Hendrickson, James B., et al., "Triphenyl Phosphine Ditriflate: A General Oxygen Activator", Tetrahedron Letters, No. 4, 1975, ppg 277–280.
Brewster, Hames H., et al., "Dehydrations with Aromatic Sulfonyl Halides. A Convenient Method for the Preparation of Esters", J. Am. Chem. Soc., vol 77, 1995, ppg 6214–6215.
Grieco, Paul A., et al., "Direct Conversion of Carboxylic Acids Into Amides", J. Org. Chem., vol. 44, No. 16, 1979, ppg 2945–2947.
Collum, David B., et al., "A New Synthesis of Amides and Macrocylic Lactams", J. Org. Chem., vol 43, No. 22, 1978, ppg 4393–4394.
Bald, Edward, et al., "A Facile Synthesis of Carboxyamides by Using 1–methyl–2–halopyridinium Iodides as Coupling Reagents", Chemistry Letters, 1975, ppg 1163–1166.
McCarty, F.J., et al., "Synthesis and Pharmacology of a Series of 1–aralkyl–3–butenylamines" J. Med. Chem., vol 11, 1968, ppg 534–541.
Meyers, A.I., et al., "The Synthesis of Aracemic 4–Substituted Pyrrolidinones and 3–Substituted Pyrrolidines. An Asymmetric Synthesis of (–)–Rolipram", J. Org. Chem., 1993, vol 58, ppg 36–42.
Duplantier, A. J., et al., "Biarylcarboxylic Acids and –amides: Inhibition of Phosphodiesterase Type IV versus [$^3$H]Rolipram Binding Activity and Their Relationship to Emetic Behavior in the Ferret", J. Med. Chem., 1996, vol 39, ppg 120–125.
Jones, Jr., W. J., et al., "A Convenient Synthesis of Dengibsin", J. Org. Chem., 1996, vol 61, ppg 3920–3922.
Lindner, N.L., et al., "Formation of Columnar and Cubic Mesophases by Calamitic Molecules: Novel Amphotropic Biphenyl Derivatives", J. Phys. Chem. B, 1998, vol 102, ppg 5261–5273.
Ashton, M.J., "Selective Type IV Phosphodiesterase Inhibitors as Antiasthmatic Agents. The Syntheses and Biological Activities of 3–(Cyclopentyloxy)–4–methoxybenzamides and Analogues", J. Med. Chem., 1994, vol 37, ppg 1696–1703.
Schoenberg A., et al., "Palladium–Catalyzed Formylation of Aryl, Heterocyclic, and Vinylic Halides", Journal of the American Chemical Society, 96:25, Dec. 11, 1974, ppg 7761–7764.
Ley, S.V., et al., "Polyurea–encapsulated palladium(II) acetate: a robust and recyclable catalyst for use in conventional and supercritical media", Chem. Comm. , 2002, ppg 1134–1135.
Lai, C–H., et al., "Intermolecular Diels–Alder Reactions of Brominated Masked o–Benzoquinones with Electron–Deficient Dienophiles. A Detour Method to Synthesize Bicyclo [2.2.2]octenones from 2–Methoxphenols", J. Org. Chem., 2002, vol 67, ppg 6493–6502.
Reid, Peter, "Roflumilast Altana Pharma", Current Opinion in Investigational Drugs, 2002, vol 3, no 8, ppg 1165–1170.

* cited by examiner

*Primary Examiner*—Paul J. Killos
(74) *Attorney, Agent, or Firm*—Edgar E. Spielman, Jr.

(57) ABSTRACT

Roflumilast and new key intermediates therefor are prepared by processes involving use of carbonylation technology. Good overall yields can be achieved using available starting materials. The starting material for the process can be catechol, an o-$R_1$-phenol, an o-$R_1$-p-X-phenol, or a 1-X-3-$R_1$-4-$R_2$-benzene, where $R_1$, is a $C_{1-6}$ alkoxy, $C_{3-7}$ cycloalkoxy, $C_{3-7}$ cycloalkylmethoxy, or benzyloxy group, or a $C_{1-4}$ alkoxy group which is completely or partially substituted by fluorine; $R_2$ is a $C_{1-4}$ alkoxy group which is completely or partially substituted by fluorine; and X is Cl, Br, or I.

51 Claims, 4 Drawing Sheets

PROCESS FOR PRODUCTION OF FLUOROALKOXY-SUBSTITUTED BENZAMIDES AND THEIR INTERMEDIATES

BACKGROUND

Roflumilast (CAS 162401-32-3) is a member of a class of fluoroalkoxy-substituted benzamides developed by BYK Gulden Lomberg Chemische Fabrik GmbH. See U.S. Pat. No. 5,712,298 to Hermann Amschler. The compounds are indicated to be useful as phosphodiesterase inhibitors. Roflumilast itself is an once-daily oral phosphodiesterase inhibitor in phase III trials to treat asthma and pulmonary obstructive disease. Another indication of dermatitis is still in preclinical stage. The chemical name of roflumilast is 3-(cyclopropylmethoxy)-N-(3,5-dichloro4-pyridiny)-4-(difluoromethoxy)benzamide.

The best known published route to roflumilast and its congeners is a six-step process with an overall yield of only 4 percent. Another previously-known synthetic route is a five-step procedure involving a Reimer-Tiemann reaction. Attempts to carry out this synthetic route failed; the particular Reimer-Tiemann reaction could not be reproduced.

A need exists for a practical process for production of roflumilast and its congeners capable of forming the products in good overall yields using available starting materials.

This invention is deemed to fulfill this need in an efficient manner.

BRIEF SUMMARY OF THE INVENTION 3,4-Disubstituted benzoic acid esters, 3,4-disubstituted benzoic acids, and 3,4-disubstituted benzoyl chlorides or bromides, in which the substituent in the 3-position, $R_1$, is a $C_{1-6}$ alkoxy, $C_{3-7}$ cycloalkoxy, $C_{3-7}$ cycloalkylmethoxy, or benzyloxy group, or a $C_{1-4}$ alkoxy group which is completely or partially substituted by fluorine, and in which the substituent in the 4-position, $R_2$, is a $C_{1-4}$ alkoxy group which is completely or partially substituted by fluorine, are useful intermediates for the preparation of many of the fluoroalkoxy-substituted benzamides described in U.S. Pat. No. 5,712,298 to Hermann Amschler. This invention thus provides, inter alia, processes for the preparation of such 3,4-disubstituted benzoic acid esters, 3,4-disubstituted benzoic acids, and 3,4-disubstituted benzoyl chlorides or bromides.

This invention provides a process for the preparation of a 3,4-disubstituted benzoyl compound in which the substituent in the 3-position, $R_1$, is a $C_{1-6}$ alkoxy, $C_{3-7}$ cycloalkoxy, $C_{3-7}$ cycloalkylmethoxy, or benzyloxy group, or a $C_{1-4}$ alkoxy group which is completely or partially substituted by fluorine, and in which the substituent in the 4-position, $R_2$, is a $C_{1-4}$ alkoxy group which is completely or partially substituted by fluorine, which process comprises:

A) alkylating an ortho-$R_1$-substituted para-halophenol in which the para-halo substituent is a chloro, bromo, or iodo substituent with an alkylating agent which is a $C_{1-4}$ monobaloalkane in which the halo substituent is chloro, bromo, or iodo, and in which said monohaloalkane is otherwise completely or partially substituted by fluorine, to form a product comprised of a 1-halo-3,4-disubstituted benzene in which the substituent in the 3-position is $R_1$, and in which the substituent in the 4-position is $R_2$;

B) carbonylating 1-halo-3,4-disubstituted benzene from A) with carbon monoxide to form a product comprised of a 3,4-disubstituted benzoyl compound in which the substituent in the 3-position is $R_1$, and in which the substituent in the 4-position is $R_2$.

In further embodiments, 3,4-disubstituted benzoyl compound from B) is converted using aniline, 4-aminopyridine, aniline which is substituted by $R_{31}$, $R_{32}$, and $R_{33}$, or 4-aminopyridine which is substituted by $R_{34}$, $R_{35}$, $R_{36}$, and $R_{37}$ wherein:

$R_{31}$, is hydroxyl, halogen, cyano, carboxyl, trifluoromethyl, $C_{1-4}$ alkyl, $C_{1-4}$ alkoxy, $C_{1-4}$ alkoxycarbonyl, $C_{1-4}$ alkylcarbonyl, $C_{1-4}$ alkylcarbonyloxy, amino, mono- or di-$C_{1-4}$ alkylamino or $C_{1-4}$ alkylcarbonylarmino;

$R_{32}$ is hydrogen, hydroxyl, halogen, amino, trifluororethyl, $C_{1-4}$ alkyl, or $C_{1-4}$ alkoxy;

$R_{33}$ is hydrogen, halogen, amino, $C_{1-4}$ alkyl, or $C_{1-4}$ alkoxy;

$R_{34}$ is hydroxyl, halogen, cyano, carboxyl, $C_{1-4}$ alkyl, $C_{1-4}$ alkoxy, $C_{1-4}$ alkoxycarbonyl, or amino;

$R_{35}$ is hydrogen, halogen, amino, or $C_{1-4}$ alkyl;

$R_{36}$ is hydrogen or halogen; and $R_{37}$ is hydrogen or halogen;

into a product comprised of the resultant 3,4-disubstituted benzamide.

A preferred embodiment of this invention is a process for the preparation of a 3,4-disubstituted benzoic acid ester in which the substituent in the 3-position, $R_1$, is a $C_{1-6}$ alkoxy, $C_{3-7}$ cycloalkoxy, $C_{3-7}$ cycloalkylmethoxy, or benzyloxy group, or a $C_{1-4}$ alkoxy group which is completely or partially substituted by fluorine, and in which the substituent in the 4-position, $R_2$, is a $C_{1-4}$ alkoxy group which is completely or partially substituted by fluorine, which process comprises:

A) alkylating an ortho-$R_1$-substituted para-halophenol in which the para-halo substituent is a chloro, brormo, oriodo substituent with an alkylating agent which is a $C_{1-4}$ monohaloalkane in which the halo substituent is chloro, bromo, or iodo, and in which said monohaloalkane is otherwise completely or partially substituted by fluorine, to form a product comprised of a 1-halo-3,4-disubstituted benzene in which the substituent in the 3-position is $R_1$, and in which the substituent in the 4-position is $R_2$;

B) carbonylating 1-halo-3,4-disubstituted benzene from A) with carbon monoxide under alkaline conditions and in the presence of an alcohol to form a product comprised of a 3,4-disubstituted benzoic acid ester in which the substituent in the 3-position is $R_1$, and in which the substituent in the 4-position is $R_2$.

A preferred way of converting the 3,4-disubstituted benzoyl compound formed in B)—in this particular case a 3,4-disubstituted benzoic acid ester—to the desired 3,4-disubstituted benzamide comprises hydrolyzing 3,4-disubstituted benzoic acid ester from B) to the corresponding 3,4-disubstituted benzoic acid. 3,4-Disubstituted benzoic acid formed by the hydrolysis can be readily converted to the corresponding 3,4-disubstituted benzoyl chloride or bromide, for example by reaction with $SOCl_2$ or $SOBr_2$. Such 3,4-disubstituted benzoyl chloride or bromide can then be amidated with aniline, 4-aminopyridine, aniline which is substituted by $R_{31}$, $R_{32}$, and $R_{33}$, or 4-aminopyridine which is substituted by $R_{34}$, $R_{35}$, $R_{36}$, and $R_{37}$, wherein $R_{31}$, $R_{32}$, $R_{33}$, $R_{34}$, $R_{35}$, $R_{36}$, and $R_{37}$ are as described above, to form a product comprised of the resultant 3,4-disubstituted benzamide.

Another of the preferred embodiments of this invention is a process for the preparation of a 3,4-disubstituted benzoic acid ester in which the substituent in the 3-position, $R_1$, is a $C_{1-6}$ alkoxy, $C_{3-7}$ cycloalkoxy, $C_{3-7}$ cycloalkylmethoxy, or benzyloxy group, or a $C_{1-4}$ alkoxy group which is completely or partially substituted by fluorine, and in which the substituent in the 4-position, $R_2$, is a $C_{1-4}$ alkoxy group which is completely or partially substituted by fluorine, which process comprises:

a) halogenating (i) an ortho-$R_1$-substituted phenol to form a product comprised of (ii) an ortho-$R_1$-substituted para-halophenol in which the para-halo substituent of (ii) is a chloro, bromo, or iodo substituent;

b) alkylating ortho-$R_1$-substituted para-halophenol from a) with an alkylating agent which is a $C_{1-4}$ monohaloalkane in which the halo substituent is chloro, bromo, or iodo, and in which said monohaloalkane is otherwise completely or partially substituted by fluorine, to form a product comprised of (iii) a 1-halo-3,4-disubstituted benzene in which the substituent in the 3-position is $R_1$, and in which the substituent in the 4-position is $R_2$;

c) carbonylating 1-halo-3,4-disubstituted benzene from b) with carbon monoxide under alkaline conditions and in the presence of an alcohol to form a product comprised of (iv) an 3,4-disubstituted benzoic acid ester in which the substituent in the 3 -position is $R_1$, and in which the substituent in the 4-position is $R_2$.

As noted above, 3,4-disubstituted benzoic acid ester formed in the carbonylation reaction can readily be hydrolyzed to the corresponding 3,4-disubstituted benzoic acid. Also 3,4-disubstituted benzoic acid formed by the hydrolysis can be readily converted to the corresponding 3,4-disubstituted benzoyl chloride or bromide, for example by reaction with $SOCl_2$ or $SOBr_2$. And as also noted above, such 3,4-disubstituted benzoyl chloride or bromide can then be amidated with aniline, 4-aminopyridine, aniline which is substituted by $R_{31}$, $R_{32}$, and $R_{33}$, or 4-aminopyridine which is substituted by $R_{34}$, $R_{35}$, $R_{36}$, and $R_{37}$ wherein $R_{31}$, $R_{32}$, $R_{33}$, $R_{34}$, $R_{35}$, $R_{36}$, and $R_{37}$ are as described above, to form a product comprised of the resultant 3,4-disubstituted benzamide.

Also provided by this invention is a process for the preparation of fluoroalkoxy-substituted benzamides, which process comprises:

a) halogenating (i) an ortho-substituted phenol to form a product comprised of (ii) an ortho-substituted para-halophenol, said substituent in the ortho position of (i) and (ii) being $R_1$ wherein $R_1$ is a $C_{1-6}$ alkoxy, $C_{3-7}$ cycloalkoxy, $C_{3-7}$ cycloalkylmethoxy, or benzyloxy group, or a $C_{1-4}$ alkoxy group which is completely or partially substituted by fluorine, and the para-halo substituent of (ii) is a chloro, bromo, or iodo substituent;

b) alkylating ortho-substituted para-halophenol from a) with an alkylating agent which is a $C_{1-4}$ monohaloalkane in which the halo substituent is chloro, bromo, or iodo, and in which said monohaloalkane is otherwise completely or partially substituted by fluorine, to form a product comprised of (iii) a 1-halo-3,4-disubstituted benzene in which the substituent in the 3-position is $R_1$, and in which the substituent in the 4-position is $R_2$ wherein $R_2$ is a $C_{1-4}$ alkoxy group which is completely or partially substituted by fluorine;

c) carbonylating 1-halo-3,4-disubstituted benzene from b) with carbon monoxide under alkaline conditions and in the presence of an alcohol to form a product comprised of (iv) an 3,4-disubstituted benzoic acid ester in which the substituent in the 3-position is $R_1$, and in which the substituent in the 4-position is $R_2$, and hydrolyzing said ester to the corresponding 3,4-disubstituted benzoic acid;

d) converting 3,4-disubstituted benzoic acid ester from c) to (v) 3,4-disubstituted benzoyl chloride or bromide; and e) amidating 3,4-disubstituted benzoyl chloride or bromide from d) with aniline, 4-aminopyridine, aniline which is substituted by $R_{31}$, $R_{32}$, and $R_{33}$, or 4-aminopyridine which is substituted by $R_{34}$, $R_{35}$, $R_{36}$, and $R_{37}$ wherein $R_{31}$, $R_{32}$, $R_{33}$, $R_{34}$, $R_{35}$, $R_{36}$, and $R_{37}$ are as described above, to form a product comprised of the resultant 3,4-disubstituted benzamide.

Novel key intermediates making possible the process technology of this invention are o-(cycloalkylmethoxy)-p-halophenols in which the cycloalkylmethoxy group is a $C_{3-7}$ cycloalkylmethoxy group, and in which the halo substituent is a chlorine, bromine or iodine atom, especially o-(cyclopropylmethoxy)-p-bromophenol, and 1-halo-3,4-disubstituted benzenes in which the halo substituent in the 1-position is a chlorine, bromine, or iodine atom, in which the substituent in the 3-position, $R_1$, is a $C_{1-6}$ alkoxy, $C_{3-7}$ cycloalkoxy, $C_{3-7}$ cycloalkylmethoxy, or benzyloxy group, or a $C_{1-4}$ alkoxy group which is completely or partially substituted by fluorine, and in which the substituent in the 4-position, $R_2$, is a $C_{1-4}$ alkoxy group which is completely or partially substituted by fluorine, especially 1-bromo-3-(cyclopropylmethoxy)-4-difluoromethoxybenzene.

Another embodiment of this invention is a process which comprises converting a 1-halo-3-$R_1$-4-$R_2$-substituted benzene in which the $R_1$ and $R_2$ substituents are as described above, and in which the halo substituent is a chlorine, bromine or iodine atom, to a 3-$R_1$-4-$R_2$-substituted benzamide in which the amide functionality has the formula— CONHR, where R is a phenyl group optionally substituted by $R_{31}$, $R_{32}$, and $R_{33}$, or a 4-pyridyl group optionally substituted by $R_{34}$, $R_{35}$, $R_{36}$ and $R_{37}$, where $R_{31}$, $R_{32}$, $R_{33}$, $R_{34}$, $R_{35}$, $R_{36}$ and $R_{37}$ are as described above. There are various ways by which this conversion can be accomplished. One way is a process which comprises:

1) subjecting a 1-halo-3-$R_1$-4-$R_2$-substituted benzene in which the $R_1$ and $R_2$ substituents are as described above, and in which the halo substituent is a chlorine, bromine or iodine atom, to carbonylation to form a 3-$R_1$-4-$R_2$-substituted benzene in which the 1-position contains carboxy functionality, and optionally transforming the carboxy functionality, such that there is produced a product comprised of (i) a 3-$R_1$-4-$R_2$-substituted benzoic acid ester, (ii) a 3 -$R_1$-4-$R_2$-substituted benzoic acid, (iii) an alkali or alkaline earth metal salt of a 3-$R_1$-4-$R_2$-substituted benzoic acid, or (iv) a 3-$R_1$-4-$R_2$-substituted benzoyl chloride or bromide; and 2) amidating (i), (ii), (iii) or (iv), or a mixture of any two or more of (i), (ii), (iii) and (iv) with aniline, 4-aminopyridine, aniline which is substituted by $R_{31}$, $R_{32}$, and $R_{33}$, or 4-aminopyridine which is substituted by $R_{34}$, $R_{35}$, $R_{36}$, and $R_{37}$, wherein $R_{31}$, $R_{32}$, $R_{33}$, $R_{34}$, $R_{35}$, $R_{36}$, and $R_{37}$ are as described above, to form a product comprised of the resultant 3,4-disubstituted benzamide.

The carboxy functionality referred to in 1) above is an esterified carboxyl group (—COOR'), a carboxyl group (—COOH), a carboxyl group that has been metal cation (—COOM or —COOM$_{0.5}$), or a carbonyl chloride or carbonyl bromide group (—COCl or —COBr). Thus the transforming of the carboxy functionality referred to in 1) above means converting one such carboxy functionality to another such carboxy functionality, which conversions are within the knowledge and skill of those of ordinary skill in the art.

Another way of effecting the conversion of a 1-halo-3-$R_1$-4-$R_2$-substituted benzene to a 3-$R_1$-4-$R_2$-substituted benzamine in which the amide functioality has the formula —CONHR is a process which comprises subjecting a 1-halo-3-$R_1$-4-$R_2$-substituted benzene in which the $R_1$ and $R_2$ substituents are as described above, and in which the halo substituent is a chlorine, bromine or iodine atom, to carbonylation in the presence of aniline, 4-aminopyridine, aniline which is substituted by $R_{31}$, $R_{32}$, and $R_{33}$, or 4-aminopyridine which is substituted by $R_{34}$, $R_{35}$, $R_{36}$, and $R_{37}$, wherein $R_{31}$, $R_{32}$, $R_{33}$, $R_{34}$, $R_{35}$, $R_{36}$, and $R_{37}$ are as described above, to form a product comprised of the resultant 3,4-disubstituted benzamide. Conditions that may be used for carrying out this reaction are referred to in A. Schoenberg and R. F. Heck, *J. Org. Chem.*, 1974, 39, 3327. See also Example 5, infra.

Other embodiments and features of this invention will be still further apparent from the ensuing description and appended claims.

FURTHER DETAILED DESCRIPTION OF THE INVENTION

To facilitate the description, unless otherwise specified: $R_1$ is a $C_{1-6}$ alkoxy, $C_{3-7}$ cycloalkoxy, $C_{3-7}$ cycloalkylmethoxy, or benzyloxy group, or a $C_{1-4}$ alkoxy group which is completely or partially substituted by fluorine; $R_2$ is a $C_{1-4}$ alkoxy group which is completely or partially substituted by fluorine; $R_3$ is an alkyl group; $R_4$ is phenyl, a phenyl group substituted by $R_{31}$, $R_{32}$, and $R_{33}$ as described above, 4-pyridyl, or a 4-pyridyl group substituted by $R_{34}$, $R_{35}$, $R_{36}$, and $R_{37}$ as described above; and X is Cl, Br, or I.

Figure 1:
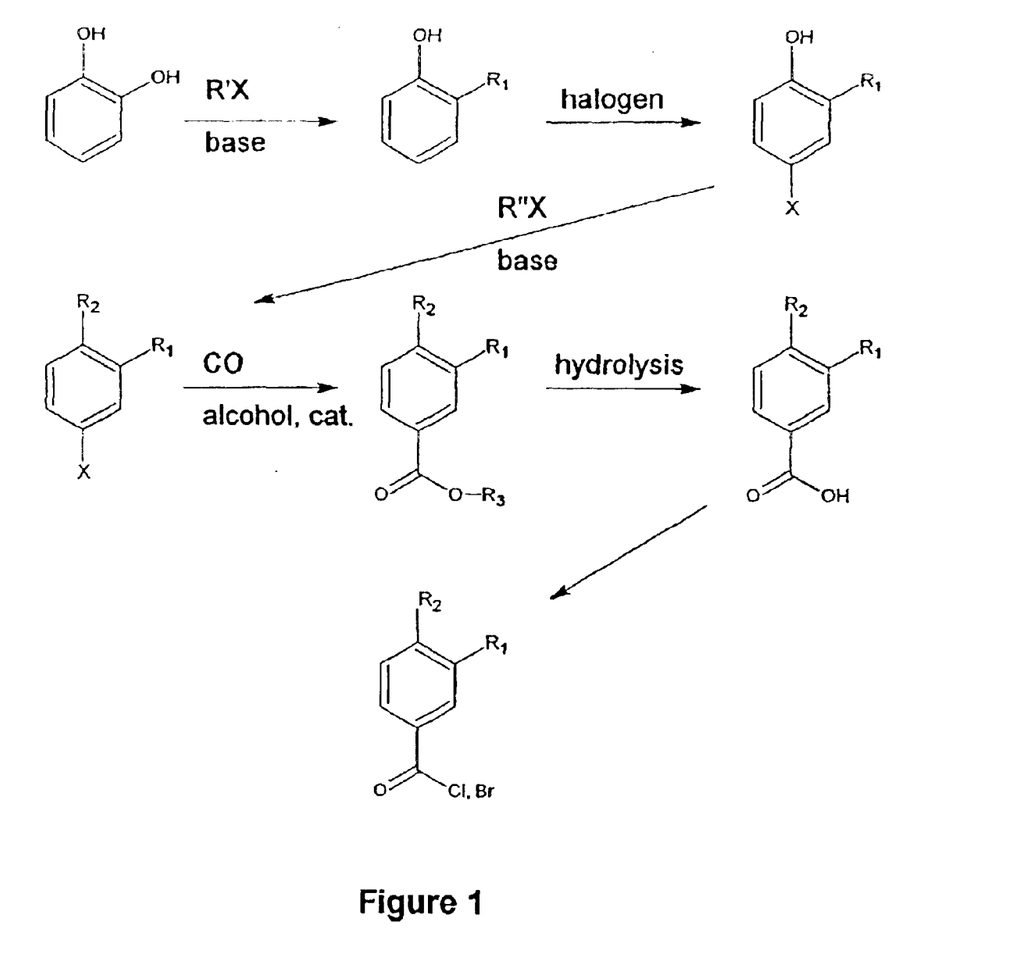
FIG. 1 depicts using general formula, reactions involved in forming a 3,4-disubstituted benzoic acid ester, optionally a 3,4-disubstituted benzoic acid and optionally a 3,4-disubstituted benzoyl chloride or bromide by process technology of this invention.

Referring to FIG. 1, it can be seen that an initial reactant in a process for producing a 3,4-disubstituted benzoic acid ester, optionally a 3,4-disubstituted benzoic acid and optionally a 3,4-disubstituted benzoyl chloride or bromide pursuant this invention where $R_1$ is the substituent in the 3-position and $R_2$ is the substituent in the 4-position, can be catechol, an o-$R_1$-phenol, an o-$R_1$-p-X-phenol, or a 1-X-3-$R_1$-4-$R_2$-benzene. The full sequence of these reactions is depicted in FIG. 1 The reactions depicted therein involve alkylation of catechol with R'X, typically in the presence of a strong base and an alcohol (e.g., NaOH in EtOH) to form o-$R_1$-phenol. Halogenation of o-$R_1$-phenol, typically in a suitable halogenation solvent, produces o-$R_1$-p-X-phenol. Alkylation of o-$R_1$-p-X-phenol with R"X, typically in a caustic solution in an ether with a catalytic amount of quaternary ammonium halide phase transfer catalyst, forms 1-X-3-$R_1$-4-$R_2$-benzene. Carbonylation of 1-X-3-$R_1$-4-$R_2$-benzene typically in an alcoholic medium using a carbonylation catalyst system and pressurized carbon monoxide forms 3-$R_1$-4-$R_2$ benzoic acid ester. Hydrolysis of the ester yields 3-$R_1$-4-$R_2$ benzoic acid. Conversion of 3-$R_1$-4-$R_2$benzoic acid to 3-$R_1$-4-$R_2$benzoyl chloride or bromide is typically conducted using thionyl chloride or bromide.

Figure 2:
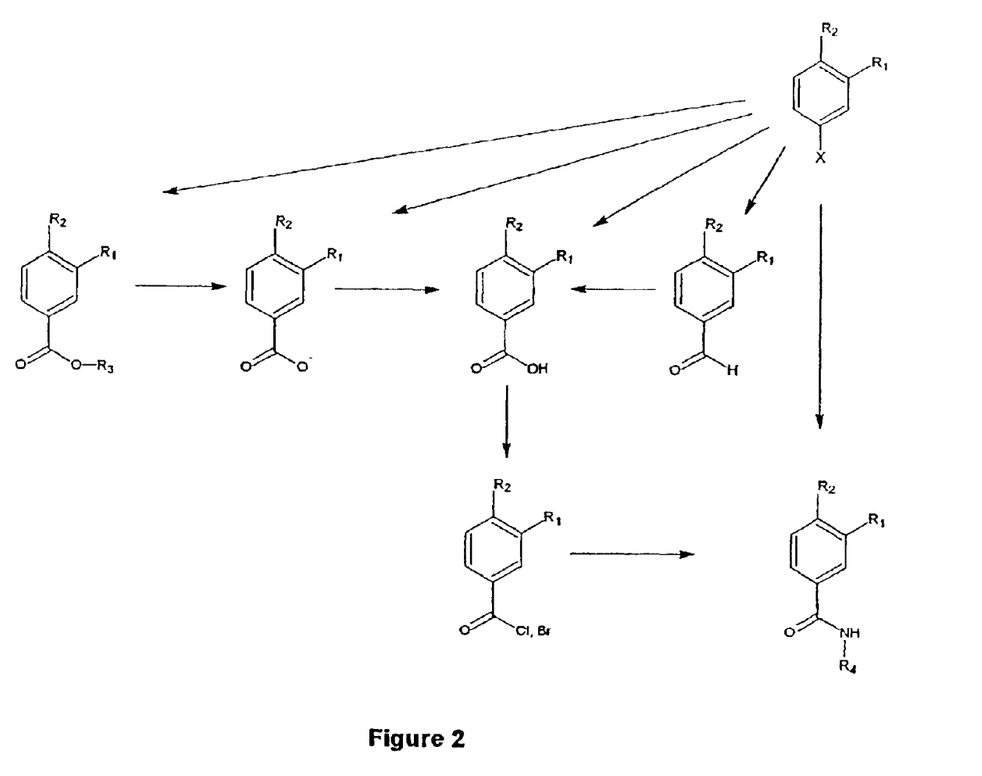
FIG. 2 depicts using general formula, various reactions that can be used in forming a 3,4-disubstituted benzamide by process technology of this invention.
Figure 3:
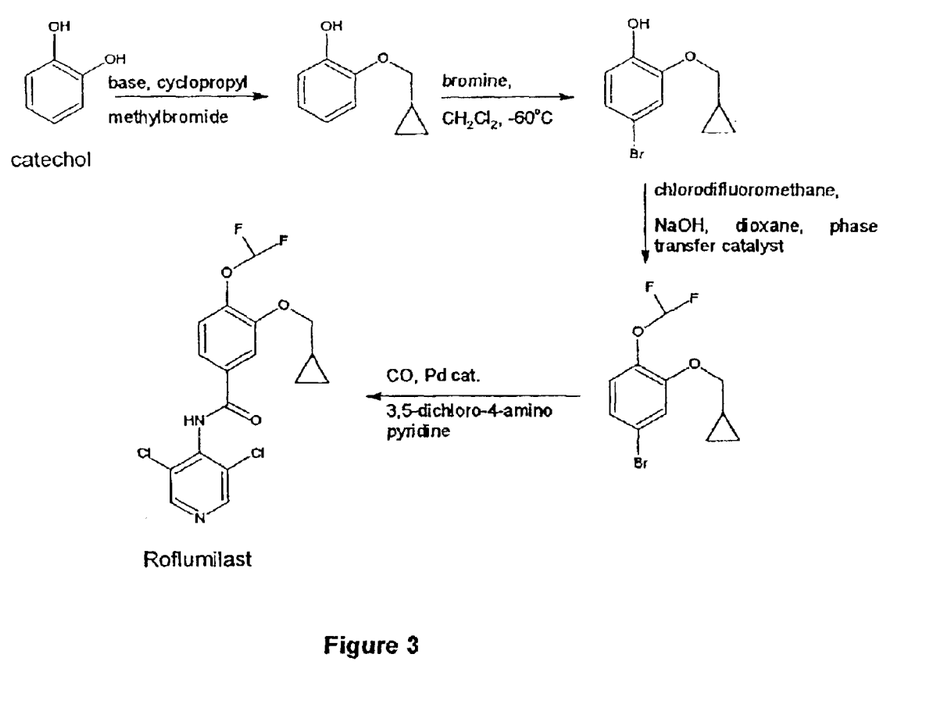
FIG. 3 shows a preferred overall synthesis route to formation of roflumilast.
Figure 4:
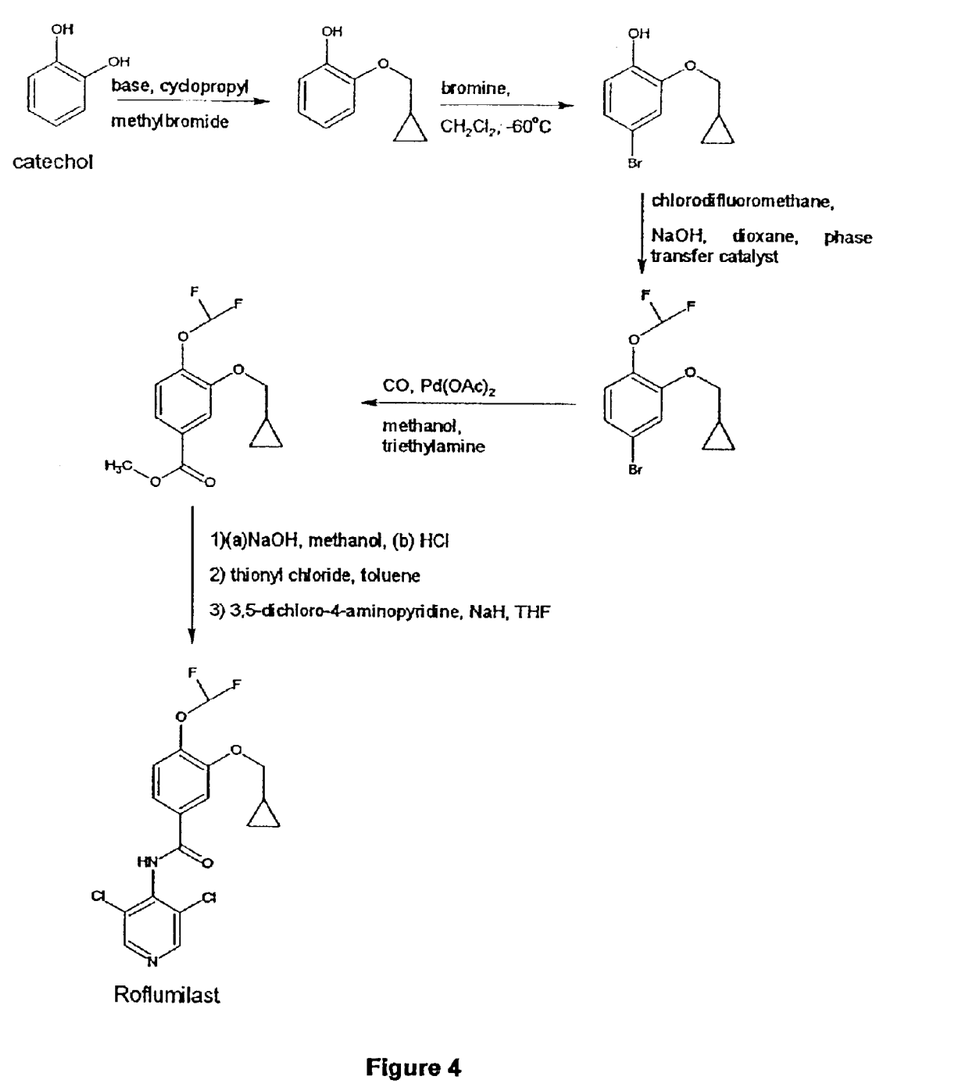
FIG. 4 shows another preferred overall synthesis route to formation of roflumilast.

Referring to FIG. 2 various ways of converting a 1-halo-3-$R_1$-4-$R_2$-substituted benzene, preferably formed as described above, to a 3-$R_1$-4-$R_2$-substituted benzamide are depicted. A preferred route involves subjecting a 1-halo-3-$R_1$-4-$R_2$-substituted benzene to carbonylation in the presence of an alcohol, typically a $C_{1-6}$ alkanol, to form a 3-$R_1$-4-$R_2$-substituted benzoic acid ester. In other words, in this route a 3-$R_1$-4-$R_2$-substituted benzene in which the 1-position contains as the carboxy functionality, an esterified carboxyl group (—COOR'). Preferably, the ester group is hydrolyzed to the free carboxyl group which is then converted to the acyl chloride or bromide group. This in turn is amidated to form the desired substituted benzamide product.

Another way of forming the amidated product is to conduct the carbonylation with carbon monoxide under a suitably elevated pressure (preferably a palladium-catalyzed carbonylation) in an acidic aqueous medium to form the carboxylic group directly, and then convert to the carboxyl group to the acyl chloride or bromide group (e.g., using thionyl chloride or bromide), which in turn is amidated to form the desired substituted benzamide product. If desired, the esterified carboxyl group can be saponified to form an alkali or alkaline earth metal salt of a 3-$R_1$-4-$R_2$-substituted benzoic acid, which in turn can be acidified to form the corresponding 3-$R_1$-4-$R_2$-substituted benzoic acid. Ensuing conversion of the carboxyl group to the acyl chloride or bromide group (e.g., using thionyl chloride or bromide) followed by amidation can yield the desired substituted benzamide product. Alternatively, the carbonylation (preferably a palladium-catalyzed carbonylation) can be conducted in the presence of an aqueous medium containing alkali metal base to form the alkali metal carboxylate salt, which is acidified to form the carboxyl group which then is converted to the acyl chloride or bromide group, which in turn is amidated to form the desired product. These and other ways of transforming the carbonylation product comprised of a 3,4-disubstituted benzoyl compound in which the substituent in the 3-position is $R_1$, and in which the substituent in the 4-position is $R_2$ to desired end product (which is preferably roflumilast itself) using aniline, 4-aminopyridine, aniline which is substituted by $R_{31}$, $R_{32}$, and $R_{33}$, or 4-aminopyridine which is substituted by $R_{34}$, $R_{35}$, $R_{36}$, and $R_{37}$ will now, from a reading of this disclosure, be readily apparent to one of ordinary skill in this art.

The carbonylation of aryl halides with carbon monoxide can be catalyzed by use of various carbonylation catalyst systems based on metals of Groups 8,9, or 10, such as nickel, cobalt, iron, rhodium and palladium. The literature contains a number of review articles on carbonylation of aryl halides with carbon monoxide, and some of these references are summarized and discussed in *New Syntheses With Carbon Monoxide*, edited by J. Falbe, Springer-Verlag Publishers, New York, 1980 at pages 294–296. Preferably, the carbonylation is conducted using a palladium-based catalytic system such as palladium metal, or a palladium salt such as a palladium (II) halide or carboxylate salt, most preferably in the presence of a suitable organic phosphine ligand, such as a triarylphosphine, an alkyl(diaryl)phosphine, or a cycloalkyl(diaryl)phosphine.

Typical conditions for effecting the reactions referred to in the accompanying Drawings are as follows:

a) Alkylation of catechol is typically conducted in a solvent such as EtOH at a temperature in the range of about 25 to about 150° C. in the presence of a strong base such as NaOH. The proportions used are not critical as long as there is sufficient alkylating agent to achieve a suitable conversion of the catechol to phenol substituted in the ortho position by $R_1$(alkoxy, cycloalkoxy, cycloalkylmethoxy, or benzyloxy).

b) Halogenation of the substituted phenol formed in a) is typically conducted in a solvent such as $CH_2Cl_2$ at a temperature in the range of about −100 to about 50° C. Typically a stoichiometric amount of halogen is used so as to avoid over-halogenation.

c) Alkylation of the halogenated substituted phenol formed in b) is typically conducted in a solvent such as dioxane at a temperature in the range of about 25 to about 150° C. in the presence of a strong base such as NaOH. The proportions used are not critical as long as there is sufficient alkylating agent ($C_{1-4}$ alkyl chloride in which the alkyl group is completely or partially substituted by fluorine) to achieve a suitable conversion of the hydroxyl group of the halogenated substituted phenol to a $C_{1-4}$ alkoxy group which is completely or partially substituted by fluorine.

d) The conditions used in the carbonylation step have been described above and will vary to some extent depending upon whether the desired product is to be an aromatic ester, carboxylic acid, carboxylic acid salt, or aldehyde. Thus, to form the ester a lower alcohol is used along with a suitable Group 8,9, or 10 carbonylation catalyst, and carbon monoxide at a pressure in the range of about 0 to about 3000 psig and a temperature in the range of about 50 to about 200° C. To form the free carboxylic acid, the same conditions are typically used except that no alcohol is used. If desired, an inert solvent such as aqueous THF can be used. To form the carboxylic acid salt, the same general carbonylation conditions can be used with the exception that the reaction is performed in the presence of at least a stoichiometric amount of caustic solution. To form the aromatic aldehyde, the reaction is carried out under the same general conditions but using CO and a reducing agent, such as $H_2$, HCOONa, or trialkylsilane.

e) When an ester is formed in d), it is preferred to hydrolyze the ester functionality to a carboxyl group. Such hydrolysis is typically conducted in the presence of NaOH aqueous solution at a temperature in the range of about 0 to about 150° C. When an aromatic aldehyde is formed in d), it is preferred to oxidize the aldehyde to the corresponding carboxylic acid by use of a suitable oxidizing agent such as bleach, sodium perborate, or air. This reaction is typically carried out at a temperature in the range of about 0 to about 150° C.

f) The aromatic carboxylic acid formed in e) is preferably treated with a reagent such as thionyl chloride or bromide. This reaction is usually carried out at a temperature in the range of about 0 to about 150° C. At least a stoichiometric amount of the thionyl chloride or thionyl bromide should be employed. The product of this reaction is the substituted acyl halide.

g) The substituted acyl halide formed in f) is typically converted to the desired substituted benzamide product by reacting the acyl halide with aniline, 4-aminopyridine, aniline which is substituted by $R_{31}$, $R_{32}$, and $R_{33}$, or 4-aminopyridine which is substituted by $R_{34}$, $R_{35}$, $R_{36}$, and $R_{37}$.

h) An alternative direct route involves converting the alkylated halogenated phenol formed in c) to the desired substituted benzamide product by conducting a carbonylation in the presence of aniline, 4-aminopyridine, aniline which is substituted by $R_{31}$, $R_{32}$, and $R_{33}$, or 4-aminopyridine which is substituted by $R_{34}$, $R_{35}$, $R_{36}$, and $R_{37}$. Such a reaction is performed using carbon monoxide at a pressure in the range of about 0 to about 3000 psig and a temperature in the range of about 0 to about 200° C. using a suitable Group 8,9 or 10 metal carbonylation catalyst.

The following non-limiting Examples illustrate ways of practicing this invention.

EXAMPLE 1

Preparation of 2-cyclopropylmethoxyphenol

Catechol (550 g, Fw=110.11, 5.00 mol) and NaOH (Prilled, 100 g, Fw=40.00, 5.0 mol) were added to a 5-L, 4-neck, R-B flask under nitrogen. EtOH (anhydrous, 2 L) was added and the mixture was agitated for 1 hour. Note: Exothermic reaction! Temperature reached 58° C. before dropping back to 47° C. and it is like a chocolate milk. Bromomethylcyclopropane (Lancaster, 790 g, Fw=135.00, 5.85 mol) was added slowly via addition funnel over 1.5 hours. After the addition of the bromide, the mixture was heated to reflux at 79–81 ° C. for 24 hours. EtOH was stripped under reduced pressure and $H_2O$ (800 mL) was added to dissolve the solid. The aqueous layer was extracted with $CH_2Cl_2$ (2×400 mL) and the combined organic layers were washed with $H_2O$ (300 mL). Evaporation of the solvent of the organic phase under reduced pressure gave a brown syrup (740 g). Vacuum distillation at 90–105° C. (overhead) at 1 mmHg gave four fractions and catechol was present in each fraction. However, catechol solidified upon standing. Four fractions were combined and were mixed with hexanes (500 mL). Solid (mainly catechol) was filtered and rinsed with hexanes. Results and conditions of the initial fractionation are summarized Table 1.

TABLE 1

| Fraction | Pressure, mm-Hg | Overhead, ° C. | Skin, ° C. | Wt. g | GC purity, area % | | |
|---|---|---|---|---|---|---|---|
| | | | | | catechol | monoether | Diether |
| 1 | 0.8–0.95 | 30–>90 | 180–>210 | 14.9 | 17.3 | 75.5 | 0.6 |
| 2 | 0.75–0.8 | 90–>98 | 210–>212 | 86.8 | 8.0 | 87.4 | 1.8 |
| 3 | 0.75–0.95 | 98–>102 | 212–>213 | 435.3 | 6.7 | 85.3 | 5.2 |
| 4 | 0.95 | 102–>110 | 213–>218 | 110.0 | 0.9 | 40.7 | 46.0 |
| Bottom | | | | 67.4 | 0 | 2.0 | 58.0 |

The filtrate was concentrated by rotary evaporation. The residue was redistilled under vacuum, the results and conditions of which are summarized in Table 2.

TABLE 2

| Fraction | Pressure, mm-Hg | Overhead, °C. | Skin, °C. | Wt. g | GC purity, area % | | |
|---|---|---|---|---|---|---|---|
| | | | | | catechol | monoether | Diether |
| 1 | 0.1 | 58->71 | 199->197 | 16.3 | 0 | 96.6 | |
| 2 | 0.1 | 71->76 | 196->198 | 31.8 | 0 | 96.7 | 0.5 |
| 3 | 0.1–0.2 | 76->82 | 198->205 | 334.6 | 0 | 94.6 | 4.2 |
| 4 | 0.2 | 82->96 | 205->220 | 28.5 | 0 | 2.2 | 88.2 |
| Bottom | | | | 21.9 | 0 | 0 | 65.4 |

*Catechol was broad and not integrated. NMR still showed some unreacted catechol.

EXAMPLE 2
Preparation of 1-bromo-3-cyclopropylmethoxy-4-difluoromethoxybenzene A mixture of 2-cyclopropylmethoxyphenol (96 area % by GC, 285 g, Fw=164.20, 1.666 mol) and $CH_2Cl_2$ (2.5 L) in a 5-L reactor was cooled to −60° C. with a dry ice/acetone bath. A mixture of bromine (277 g, Fw=159.81, 1.733 mol) in $CH_2Cl_2$ (280 mL) was added at −55 to −60° C. over 30 minutes. The reaction mixture was slowly warmed to −5° C. over 1.5 hours and was then quenched with a $K_2S_2O_3$ solution (1 L). After stirring for 10 min, the organic phase was separated and was dried over $MgSO_4$. GC analysis showed 85 area % purity. Evaporation of the solvent under reduced pressure at 70° C. gave a dark oil (388.2 g) in 92% crude yield or 81.5% yield adjusted to GC area %.

A mixture of crude 4-bromo-2-cyclopropylmethoxyphenol (388 g) and $(n-Bu)_4NBr$ (20 g) in dioxane (2.0 L) was heated to 65° C. Aqueous caustic solution (40%, 294 g) was added and the temperature was raised to 80° C. Chlorodifluoromethane was added below the surface via a 12 gauge needle and $CF_2HCl$ was rapidly absorbed. After about 70 minutes, the absorption of gas ceased and reaction temperature dropped to 77° C. About 184 g of chlorodifluoromethane (Fw=86.47, 2.128 mol) had been added. GC analysis of an aliquot indicated the disappearance of the starting material. The mixture was cooled to room temperature and was quenched with water (1.2 L) under $CF_2HCl$ atmosphere. Extraction with hexanes (2×750 mL) and the combined hexanes extracts were washed with water (1 L). The aqueous layer was back-extracted with hexanes (500 mL) and the combined organic extracts were dried ($MgSO_4$) and filtered. Evaporation of the solvent under reduced pressure gave a brown oil (about 457 g). GC analysis showed 75 area % purity. The crude yield was 98% or 86% adjusted to GC area %. The crude product was distilled over a 5-plate, Older-Shaw column at 1.0 mm-Hg at 107–113° C. (overhead). Results and conditions are given in Table 3.

TABLE 3

| Fraction | Pressure | Overhead, °C. | Skin, °C. | Wt. g | GC purity, area % | |
|---|---|---|---|---|---|---|
| | | | | | 8.54 min | 8.59 min |
| 1 | 0.9 mm | 40->107 | 250->270 | 60.7 | 66.6 | 1.8 |
| 2 | 1.0 mm | 107->113 | 270->276 | 221.8 | 91.9 | 4.1 |
| 3 | 1.1 mm | 113->112 | 276->295 | 42.5 | 83.6 | 4.2 |
| bottom | | | | 90.7 | | |

The fraction #2 was used for the next step as set forth in Example 3. The isolated yield of 1-bromo-3-cyclopropylmethoxy-4-difluoromethoxybenzene was 45.5% in two steps.

EXAMPLE 3
Preparation of 3-cyclopropylmethoxy-4-difluoromethoxybenzoic acid $Pd(OAc)_2$ (1.60 g, Fw=224.49, 7.13 mmol), $Ph_3P$ (10.0 g, Fw=262.29, 38.1 mmol), 1-bromo-3-cyclopropylmethoxy-4-difluoromethoxybenzene (221.7 g, Fw=293.11, 0.756 mol), MeOH (1 L), and $Et_3N$ (275 mL, Fw=101.19, 1.976 mol) were added to a 2-L autoclave. The autoclave was sealed and was then purged with nitrogen. The mixture was purged with CO (2×50 psig) and was pressured to 200 psig with CO. The mixture was heated at 120° C. for 3 hours and the CO was kept at 200–300 psig. Note: About 390 psig of CO was consumed. GC analysis of an aliquot showed 8.41 min (starting bromide, 0.22 area %), 9.62 min (product, 94.3%), 9.84 min (isomer, 2.42%), 11.61 min (di-ester, 1.76%) excluding the phosphine. The reaction mixture was cooled to room temperature and the CO pressure was released. The mixture was transferred to a 3-L, R-B flask and was stripped under reduced pressure to give a brown paste. Partition in toluene (1 L) and water (250 mL) and evaporation of the solvent of the organic phase gave a brown oil (240 g).

A mixture of crude ester (240 g), MeOH (625 g), and 8% NaOH solution (1250 g) was heated at 70–75° C. in a 3-L, R-B flask for 2 hours. The reaction mixture was cooled to room temperature and was washed with hexanes (3×500 mL). GC analysis of the neutral fraction gave 8 40 min (starting bromide, 1.3 area %), 8.54 min (2.2%), 11.22 min (1.1%), 12.64 min ($Ph_3P$, 90.2%), 14.54 min ($Ph_3PO$, 2.5%), and 15.15 min (0.5%). The aqueous layer was acidified with 10% HCl solution to pH=2 and was extracted with $CHCl_3$ (3×500 mL). The combined organic layers were concentrated under reduced pressure to give a brown solid (200 g). The crude acid was dissolved in $CH_3CN$ (300 mL) and petroleum ether (200 mL) was added. The mixture was stirred at 0° C. overnight. The solid was filtered and was washed with cold $CH_3CN$ (50 mL). Evaporation of solvent in vacuum at 60° C. gave a light yellow solid (122 g). GC analysis (derivatized with BSTFA, i.e., bis(trimethylsilyl)trifluoroacetamide) showed 99.7 area %. A second crop (about 25 g) was recovered and GC analysis showed about 97.6% purity. Recrystallization of the second crop in $CH_3CN$ and petroleum ether gave a white crystalline solid (16.4 g). GC analysis showed about 99.5 area %. Overall yield was 70.9%. A combined product (81 g of 1$^{st}$ crop and 16 g of 2$^{nd}$ crop) was digested in $CH_3CN$ (30 mL) and petroleum ether (100 mL) at reflux and was then cooled at room temperature. Filtration and evaporation of the residual solvent in vacuum gave a white crystalline solid (86.7 g); mp=119–119.5° C. GC analysis (derivatized with BSTFA) showed >99.95 area %. NMR assay was 99.6 wt %. Proton and C-13 NMR spectra confirmed the formation of 3-cyclopropylmethoxy-4-difluoromethoxybenzoic acid.

EXAMPLE 4

Preparation of 3,5-dichloro-4-pyridinyl-3-cyclopropylmethoxy-4-difuoromethoxybenzamide (roflumilast)

A mixture of 3-cyclopropylmethoxy-4-difluoromethoxybenzoic acid (40.0 g, Fw=258.22, 0.155 mol) and toluene (anhydrous, 225 mL) was stirred in a 500-mL,4-neck, R-B flask under nitrogen. Thionyl chloride (110 g, Fw=118.97, 0.925 mol) was added via syringe and the mixture was heated at 105° C. for 3 hours. The reaction mixture was cooled to room temperature and the excess $SOCl_2$ and toluene were evaporated under reduced pressure to dryness to yield a light yellow solid. The acid chloride solid was dissolved in THF (anhydrous, inhibitor-free, 320 mL). In another R-B flask (1-L, 4-neck), NaH (60% in mineral oil, 15.0 g, 0.375 mol) was added in a dry box. The NaH was washed with dry, inhibitor-free THF (3×50 mL) to remove the mineral oil, and THF (anhydrous, inhibitor-free, 320 mL) was added to the NaH to form a slurry. 4-Amino-3,5-dichloropyridine (27.7 g, Fw=163 01, 0.170mol) was added slowly over 1 hour to the slurry of NaH in THF. Note: The mixture bubbled seriously during the addition of the aminopyridine. The flask was connected to the nitrogen line and the acid chloride/THF solution produced earlier was slowly added via addition funnel over 35 minutes. Note: A lot of bubbling was also seen during this addition. The mixture was stirred overnight at room temperature. GC analysis of an aliquot indicated complete conversion. The mixture was acidified with 1 N HCl to pH=2. About 240 g of 1 N HCl was used. [Note: (1) Some white precipitate was formed initially. The precipitate redissolved with more HCl solution. (2) Color changed to light orange initially and then turned into light yellow. (3) The reaction mixture became a clear 2-layer solution at the end.] Phase separation and the aqueous layer was extracted with EtOAc (2×150 mL). The combined organic layers were washed with $H_2O$ (70 mL), 10% $NaHCO_3$ (70 mL), and then $H_2O$ (70 mL). [Note: The phase separation was much slower in the second water wash.] Evaporation of the solvent of the organic phase gave a light yellow solid (59.4 g, 95.1% crude yield). GC analysis of the crude product gave 15.24 min (1.12 area %), 16.11 min (97.3%), and 16.46 min (1.46%). The crude product was dissolved in isopropanol (240 g) at 80° C. The mixture was gradually cooled to 40° C. and was then cooled in ice/$H_2O$ bath. The solid was filtered in a Buchi funnel and was washed with cold isopropyl alcohol (100 mL). The solid was dried in 4 mm-Hg at 60° C. for 2 hours to gave a white, crystalline solid (small flakes, 52.4 g, 88.2% recovery and 83.9% overall yield); mp=157–57.5° C. GC analysis of the final product showed 21.6 min (0.17 area %) and 26.4 min (99.83%). NMR assay was 99.5 wt %. Proton and C-13 NMR spectra also confirmed the formation of roflumilast.

EXAMPLE 5

A mixture of 1-bromo-3-cyclopropylmethoxy-4-difluoromethoxybenzene (17.2 mmol), $PdBr_2(Ph_3P)_2$ (catalytic amount, 0.25 mmol), 4-amino-3,5-dichloropyridine (25 mmol), $Bu_3N$ (19 mmol) and optionally with an inert solvent were added to an autoclave. The autoclave was sealed and was then purged with nitrogen followed by CO. The mixture was heated under CO pressure at 120 to 150° C. for 10 hours or until complete conversion. The reaction mixture was cooled and the CO pressure was released. The mixture was extracted with EtOAc, and the extracts were washed with 20% HCl solution followed by saturated $NaHCO_3$ solution, and then water. Evaporation of the solvent of the organic phase gave a crude product. The crude product was recrystallized from isopropanol to give roflumilast as a white solid.

It is to be understood that the ingredients referred to by chemical name or formula anywhere in the specification or claims hereof, whether referred to in the singular or plural, are identified as they exist prior to coming into contact with another substance referred to by chemical name or chemical type (e.g., another reactant, a solvent, a diluent, or etc.). It matters not what preliminary chemical changes, transformations and/or reactions, if any, take place in the resulting mixture or solution or reaction medium as such changes, transformations and/or reactions are the natural result of bringing the specified reactants and/or components together under the conditions called for pursuant to this disclosure. Thus the reactants and other materials are identified as ingredients to be brought together in connection with performing a desired chemical reaction or in forming a mixture to be used in conducting a desired reaction. Also, even though the claims hereinafter may refer to substances, components and/or ingredients in the present tense ("comprises", "is", etc.), the reference is to the substance or ingredient as it existed at the time just before it was first contacted, blended or mixed with one or more other substances or ingredients in accordance with the present disclosure. The fact that the substance or ingredient may have lost its original identity through a chemical reaction or transformation or complex formation or assumption of some other chemical form during the course of such contacting, blending or mixing operations, is thus wholly immaterial for an accurate understanding and appreciation of this disclosure and the claims thereof. Nor does reference to an ingredient by chemical name or formula exclude the possibility that during the desired reaction itself an ingredient becomes transformed to one or more transitory intermediates that actually enter into or otherwise participate in the reaction. In short, no representation is made or is to be inferred that the named ingredients must participate in the reaction while in their original chemical composition, structure or form.

Each and every patent or other publication or published document referred to in any portion of this specification is incorporated in toto into this disclosure by reference, as if fully set forth herein.

This invention is susceptible to considerable variation in its practice. Therefore the foregoing description is not intended to limit, and should not be construed as limiting, the invention to the particular exemplifications presented hereinabove. Rather, what is intended to be covered is as set forth in the ensuing claims and the equivalents thereof permitted as a matter of law.

That which is claimed is:

1. A process for the preparation of a 3,4-disubstituted benzoyl compound in which the substituent in the 3-position, $R_1$, is a $C_{1-6}$ alkoxy, $C_{3-7}$ cycloalkoxy, $C_{3-7}$ cycloalkylmethoxy, or benzyloxy group, or a $C_{1-4}$ alkoxy group which is completely or partially substituted by fluorine, and in which the substituent in the 4-position, $R_2$, is a $C_{1-4}$ alkoxy group which is completely or partially substituted by fluorine, which process comprises:

A) alkylating an ortho-$R_1$-substituted para-halophenol in which the para-halo substituent is a chloro, bromo, or iodo substituent with an alkylating agent which is a $C_{1-4}$ monohaloalkane in which the halo substituent is chloro, bromo, or iodo, and in which said monohaloalkane is otherwise completely or partially substituted by fluorine, to form a product comprised of a 1-halo-3,4-disubstituted benzene in which the substituent in the 3-position is R₁, and in which the substituent in the 4-position is R₂; and B) carbonylating 1-halo-3,4-disubstituted benzene from A) with carbon monoxide to form a product comprised of a 3,4-disubstituted benzoyl compound in which the substituent in the 3-position is R₁, and in which the substituent in the 4-position is R₂.

2. A process as in claim 1 wherein the carbonylation in B) is a palladium-catalyzed carbonylation conducted in an acidic aqueous medium, in an aqueous medium containing an alkali metal base or an alkaline earth metal base, or in an alcoholic medium.

3. A process for the preparation of a 3,4-disubstituted benzoic acid ester in which the substituent in the 3-position, R₁, is a $C_{1-6}$ alkoxy, $C_{3-7}$ cycloalkoxy, $C_{3-7}$ cycloalkylmethoxy, or benzyloxy group, or a $C_{1-4}$ alkoxy group which is completely or partially substituted by fluorine, and in which the substituent in the 4-position, R₂, is a $C_{1-4}$ alkoxy group which is completely or partially substituted by fluorine, which process comprises:

A) alkylating an ortho-R₁-substituted para-halophenol in which the para-halo substituent is a chloro, bromo, or iodo substituent with an alkylating agent which is a $C_{1-4}$ monohaloalkane in which the halo substituent is chloro, bromo, or iodo, and in which said monohaloalkane is otherwise completely or partially substituted by fluorine, to form a product comprised of a 1-halo-3,4-disubstituted benzene in which the substituent in the 3-position is R₁, and in which the substituent in the 4-position is R₂; and B) carbonylating 1-halo-3,4-disubstituted benzene from A) with carbon monoxide under alkaline conditions and in the presence of an alcohol to form a product comprised of a 3,4-disubstituted benzoic acid ester in which the substituent in the 3-position is R₁, and in which the substituent in the 4position is R₂.

4. A process as in claim 3 further comprising hydrolyzing ester from B) to form a product comprised of said 3,4-disubstituted benzoic acid.

5. A process as in claim 4 further comprising converting 3,4-disubtituted benzoic acid from the hydrolysis into a product comprised of the corresponding 3,4-disubstituted benzoyl chloride or bromide.

6. A process as in claim 3 wherein said R₁ is a $C_{1-6}$ alkoxy group or a $C_{3-7}$ cycloalkyl methoxy group.

7. A process as in claim 3 wherein said R₁ is a $C_{3-7}$ cycloalkylmethoxy group.

8. A process as in claim 3 wherein said ortho-R₁-substituted para-halophenol is an ortho-R₁-substituted para-bromophenol.

9. A process as in claim 3 wherein said ortho-R₁-substituted para-halophenol is o-(cyclopropylmethoxy)-p-bromophenol.

10. A process as in any of claims 3–9 wherein said alkylating agent is chlorodifluoromethane.

11. A process for the preparation of a 3,4-disubstituted benzoic acid ester in which the substituent in the 3-position, R₁, is a $C_{1-6}$ alkoxy, $C_{3-7}$ cycloalkoxy, $C_{3-7}$ cycloalkyl methoxy, or benzyloxy group, or a $C_{1-4}$ alkoxy group which is completely or partially substituted by fluorine, and in which the substituent in the 4-position, R₂, is a $C_{1-4}$ alkoxy group which is completely or partially substituted by fluorine, which process comprises:

a) halogenating (i) an ortho-R₁-substituted phenol to form a product comprised of (ii) an ortho-R₁-substituted para-halophenol in which the para-halo substituent of (ii) is a chloro, bromo, or iodo substituent;

b) alkylating ortho-R₁-substituted para-halophenol from a) with an alkylating agent which is a $C_{1-4}$ monohaloalkane in which the halo substituent is chloro, bromo, or iodo, and in which said monohaloalkane is otherwise completely or partially substituted by fluorine, to form a product comprised of (iii) a 1-halo-3,4-disubstituted benzene in which the substituent in the 3-position is R₁, and in which the substituent in the 4-position is R₂ wherein R₂ is a $C_{1-4}$ alkoxy group which is completely or partially substituted by fluorine; and c) carbonylating 1-halo-3,4-disubstituted benzene from b) with carbon monoxide under alkaline conditions and in the presence of an alcohol to form a product comprised of (iv) an 3,4-disubstituted benzoic acid ester in which the substituent in the 3-position is R₁, and in which the substituent in the 4-position is R₂.

12. A process as in claim 11 further comprising hydrolyzing ester from c) to form a product comprised of the corresponding 3,4-disubstituted benzoic acid.

13. A process as in claim 12 further comprising converting 3,4-disubstituted benzoic acid from the hydrolysis into a product comprised of the corresponding 3,4-disubstituted benzoyl chloride or bromide.

14. A process as in claim 11 wherein said R₁ is a $C_{1-6}$ alkoxy group or a $C_{3-7}$ cycloalkyl methoxy group.

15. A process as in claim 11 wherein said alkylating agent is chlorodifluoromethane.

16. A process as in any of claims 11–15 wherein said R₁ is a $C_{37}$ cycloalkylmethoxy group.

17. A process as in any of claims 11–15 wherein said ortho-R₁-substiuted phenol is o-(cycloalkyl methoxy)phenol in which the cycloalkyl methoxy group is a $C_{3-7}$ cycloalkylmethoxy group, and wherein said ortho-R₁-substituted para-halophenol is o-(cycloalkylmethoxy)-p-halophenol in which the cycloalkyl methoxy group is a $C_{3-7}$ cycloalkyl methoxy group, and in which the halo substituent is a chlorine, bromine or iodine atom.

18. A process as in claim 17 wherein said halo substituent of said halophenol is a bromine atom.

19. An o-(cycloalkyl methoxy)-p-halophenol in which the cycloalkyl methoxy group is a $C_{3-7}$ cycloalkylmethoxy group, and in which the halo substituent is a chlorine, bromine or iodine atom.

20. An o-(cycloalkylmethoxy)-p-halophenol as in claim 19 in which said halo substituent is a bromine atom.

21. o-(Cyclopropylmethoxy)-p-bromophenol.

22. A 1-halo-3,4-disubstituted benzene in which the halo substituent in the 1-position is a chlorine, bromine, or iodine atom, in which the substituent in the 3-position, R₁, is a $C_{3-7}$ cycloalkoxy, $C_{3-7}$ cycloalkyl methoxy, or benzyloxy group, and in which the substituent in the 4-position, R₂, is a $C_{1-4}$ alkoxy group which is completely or partially substituted by fluorine.

23. A 1-halo-3,4-disubstituted benzene as in claim 22 in which the halo substituent in the 1-position is a bromine atom.

24. A 1-halo-3,4-disubstituted benzene as in claim 22 in which R₁ is a $C_{3-7}$ cycloalkyl methoxy group.

25. A 1-halo-3,4-disubstituted benzene as in claim 22 in which R₁ is a cyclopropylmethoxy group.

26. A 1-halo-3,4-disubstituted benzene as in claim 22 in which R₂ is a difluoromethoxy group.

27. A 1-halo-3,4-disubstituted benzene as in claim 22 in which the halo substituent in the 1-position is a bromine atom, and in which R₁ is a $C_{3-7}$ cycloalkyl methoxy group.

28. A 1-halo-3,4-disubstituted benzene as in claim 22 in which the halo substituent in the 1-position is a bromine atom, and in which R₁ is a cyclopropylmethoxy group.

29. A 1-halo-3,4-disubstituted benzene as in claim 22 in which the halo substituent in the 1-position is a bromine atom, and in which $R_2$ is a difluoromethoxy group.

30. A 1-halo-3,4-disubstituted benzene as in claim 22 in which the 1-halo-3,4-disubstituted benzene is a 1-bromo-3-(cycloalkylmethoxy)-4-difluoromethoxybenzene in which the cycloalkyl methoxy group is a $C_{3-7}$ cycloalkyl methoxy group.

31. 1-Bromo-3-(cyclopropylmethoxy)-4-difluoromethoxybenzene.

32. A process as in any of claims 11–15 wherein the carbonylation in c) is a palladium-catalyzed carbonylation.

33. A process as in claim 11 wherein said ortho-$R_1$-substituted phenol is o-(cyclopropylmethoxy)phenol, wherein said ortho-$R_1$-substituted para-halophenol is o-(cyclopropylmethoxy)-p-bromophenol, wherein said alkylating agent is chlorodifluoromethane, and wherein the carbonylation in c) is a palladium-catalyzed carbonylation.

34. A process for the preparation of fluoroalkoxy-substituted benzamides, which process comprises:
   a) halogenating (i) an ortho-substituted phenol to form a product comprised of (ii) an ortho-substituted para-halophenol, said substituent in the ortho position of (i) and (ii) being $R_1$ wherein $R_1$ is a $C_{1-6}$ alkoxy, $C_{3-7}$ cycloalkoxy, $C_{3-7}$ cycloalkyl methoxy, or benzyloxy group, or a $C_{1-4}$ alkoxy group which is completely or partially substituted by fluorine, and the para-halo substituent of (ii) is a chloro, bromo, or iodo substituent;
   b) alkylating ortho-substituted para-halophenol from a) with an alkylating agent which is a $C_{1-4}$ monohaloalkane in which the halo substituent is chloro, bromo, or iodo, and in which said monohaloalkane is otherwise completely or partially substituted by fluorine, to form a product comprised of (iii) a 1-halo-3,4-disubstituted benzene in which the substituent in the 3-position is $R_1$, and in which the substituent in the 4-position is $R_2$ wherein $R_2$ is a $C_{1-4}$ alkoxy group which is completely or partially substituted by fluorine;
   c) carbonylating 1-halo-3,4-disubstituted benzene from b) with carbon monoxide under alkaline conditions and in the presence of an alcohol to form a product comprised of (iv) an 3,4-disubstituted benzoic acid ester in which the substituent in the 3-position is $R_1$, and in which the substituent in the 4-position is $R_2$, and hydrolyzing said ester to the corresponding 3,4-disubstituted benzoic acid;
   d) converting 3,4-disubstituted benzoic acid ester from c) to (v) 3,4-disubstituted benzoyl chloride or bromide; and
   e) amidating 3,4-disubstituted benzoyl chloride or bromide from d) with aniline, 4-aminopyridine, aniline which is substituted by $R_{31}$, $R_{32}$, and $R_{33}$, or 4-aminopyridine which is substituted by $R_{34}$, $R_{35}$, $R_{36}$, and $R_{37}$, wherein $R_{31}$ is hydroxyl, halogen, cyano, carboxyl, trifluoromethyl, $C_{1-4}$ alkyl, $C_{1-4}$ alkoxy, $C_{1-4}$ alkoxycarbonyl, $C_{1-4}$ alkylcarbonyl, $C_{1-4}$ alkylcarbonyloxy, amino, mono- or di-$C_{1-4}$ alkylamino or $C_{1-4}$ alkylcarbonylamino; $R_{32}$ is hydrogen, hydroxyl, halogen, amino, trifluoromethyl, $C_{1-4}$ alkyl, or $C_{1-4}$ alkoxy; $R_{33}$ is hydrogen, halogen, amino, $C_{1-4}$ alkyl, or $C_{1-4}$ alkoxy; $R_{34}$ is hydroxyl, halogen, cyano, carboxyl, $C_{1-4}$ alkyl, $C_{1-4}$ alkoxy, $C_{1-4}$ alkoxycarbonyl, or amino; $R_{35}$ is hydrogen, halogen, amino, or $C_{1-4}$ alkyl; $R_{36}$ is hydrogen or halogen; and $R_{37}$ is hydrogen or halogen; to form a product comprised of the resultant 3,4-disubstituted benzamide.

35. A process as in claim 34 wherein the amidation of the 3,4-disubstituted benzoyl chloride or bromide from d) is effected with aniline.

36. A process as in claim 34 wherein the amidation of the 3,4-disubstituted benzoyl chloride or bromide from d) is effected with 4-aminopyridine.

37. A process as in claim 34 wherein the amidation of the 3,4-disubstituted benzoyl chloride or bromide from d) is effected with aniline which is substituted by $R_{31}$, $R_{32}$, and $R_{33}$.

38. A process as in claim 34 wherein the amidation of the 3,4-disubstituted benzoyl chloride or bromide from d) is effected with 4-aminopyridine which is substituted by $R_{34}$, $R_{35}$, $R_{36}$, and $R_{37}$.

39. A process as in claim 34 wherein the amidation of the 3,4-disubstituted benzoyl chloride or bromide from d) is effected with 4-amino-3,5-dichloropyridine.

40. A process as in any of claims 34–39 wherein said ortho-substituted phenol is o-(cyclopropylmethoxy)phenol, wherein the o-(cyclopropylmethoxy)phenol is halogenated with bromine to form a product comprised of o-(cyclopropylmethoxy)-p-bromophenol, and wherein the alkylating agent is chlorodifluoromethane so that the product formed in said alkylation is comprised of 1-bromo-3-(cyclopropylmethoxy)-4-difluoromethoxybenzene.

41. A process as in claim 34 wherein said ortho-substituted phenol is o-(cyclopropylmethoxy)phenol, wherein the o-(cyclopropylmethoxy)phenol is halogenated with bromine to form a product comprised of 6-(cyclopropylmethoxy)-p-bromophenol, wherein the alkylating agent is chlorodifluoromethane so that the product formed in said alkylation is comprised of 1-bromo-3-(cyclopropylmethoxy)-4-difluoromethoxybenzene, wherein the carbonylation of 1-bromo-3-(cyclopropylmethoxy)-4-difluoromethoxybenzene is a palladium catalyzed carbonylation conducted in the presence of methanol so that the product formed therefrom is comprised of methyl 3-(cyclopropylmethoxy)-4-difluoromethoxybenzoate.

42. A process as in claim 41 wherein methyl 3-(cyclopropylmethoxy)-4-difluoromethoxybenzoate from said carbonylation is hydrolyzed under alkaline conditions to form a product comprised of 3-(cyclopropylmethoxy)-4-difluoromethoxybenzoic acid, and wherein 3-(cyclopropylmethoxy)-4-difluoromethoxybenzoic acid from said hydrolysis is converted by reaction with thionyl chloride to form a product comprised of 3-(cyclopropylmethoxy)-4-difluoromethoxybenzoyl chloride.

43. A process as in claim 42 wherein the amidation of said 3,4-disubstituted benzoyl chloride is effected with 4-amino-3,5-dichloropyridine.

44. A process of preparing a fluoroalkoxy-substituted benzamide, which process comprises:
   1) subjecting a 1-halo-3-$R_1$-4-$R_2$-substituted benzene wherein the halo substituent is a chlorine, bromine or iodine atom, wherein $R_1$ is a $C_{1-6}$ alkoxy, $C_{3-7}$ cycloalkoxy, $C_{3-7}$ cycloalkyl methoxy, or benzyloxy group, or a $C_{1-4}$ alkoxy group which is completely or partially substituted by fluorine, and wherein $R_2$ is a $C_{1-4}$ alkoxy group which is completely or partially substituted by fluorine, to carbonylation to form a 3-$R_1$-4-$R_2$-substituted benzene in which the 1-position contains carboxy functionality, and optionally transforming the carboxy functionality, such that there is produced a product comprised of (i) a 3-$R_1$-4-$R_2$-substituted benzoic acid ester, (ii) a 3-$R_1$-4-$R_2$-substituted benzoic acid, (iii) an alkali or alkaline earth metal salt of a 3-$R_1$-4-$R_2$-substituted benzoic acid, or (iv) a 3-$R_1$-4-$R_2$-substituted benzoyl chloride or bromide; and 2) amidating (i), (ii), (iii) or (iv), or a mixture of any two or more of (i), (ii), (iii) and (iv) with aniline, 4-aminopyridine, aniline which is substituted by $R_{31}$, $R_{32}$, and $R_{33}$, or 4-aminopyridine which is substituted by $R_{34}$, $R_{35}$, $R_{36}$, and $R_{37}$, wherein: $R_{31}$ is hydroxyl, halogen, cyano, carboxyl, trifluoromethyl, $C_{1-4}$ alkyl, $C_{1-4}$ alkoxy, $C_{1-4}$ alkoxycarbonyl, $C_{1-4}$ alkylcarbonyl, $C_{1-4}$ alkylcarbonyloxy, amino, mono- or di-$C_{1-4}$ alkylamino or $C_{1-4}$ alkylcarbonylamino; $R_{32}$ is hydrogen, hydroxyl, halogen, amino, trifluoromethyl, $C_{1-4}$ alkyl, or $C_{1-4}$ alkoxy; $R_{33}$ is hydrogen, halogen, amino, $C_{1-4}$ alkyl, or $C_{1-4}$ alkoxy; $R_{34}$ is hydroxyl, halogen, cyano, carboxyl, $C_{1-4}$ alkyl, $C_{1-4}$ alkoxy, $C_{1-4}$ alkoxycarbonyl, or amino; $R_{35}$ is hydrogen, halogen, amino, or $C_{1-4}$ alkyl; $R_{36}$ is hydrogen or halogen; and $R_{37}$ is hydrogen or halogen; to form a product comprised of the resultant 3,4-disubstituted benzamide.

45. A process as in claim 44 wherein the carbonylation is a palladium-catalyzed carbonylation in a liquid phase using carbon monoxide under superatmospheric pressure.

46. A process as in each of claim 44 or 45 wherein $R_1$ is a cyclopropylmethoxy group, $R_2$ is a bromine or iodine atom, and the amidation in 2) is effected using 4-amino-3,5-dichloropyridine so that said resultant 3,4-disubstituted benzamide is roflumilast.

47. A process of preparing a fluoroalkoxy-substituted benzamide, which process comprises subjecting a 1-halo-3-$R_1$-4-$R_2$-substituted benzene wherein $R_1$ is a $C_{1-6}$ alkoxy, $C_{3-7}$ cycloalkoxy, $C_{3-7}$ cycloalkyl methoxy, or benzyloxy group, or a $C_{1-4}$ alkoxy group which is completely or partially substituted by fluorine, and wherein the halo substituent is a chlorine, bromine or iodine atom, to carbonylation in the presence of aniline, 4-aminopyridine, aniline which is substituted by $R_{31}$, $R_{32}$, and $R_{33}$, or 4-aminopyridine which is substituted by $R_{34}$, $R_{35}$, $R_{36}$, and $R_{37}$, wherein $R_{31}$, $R_{32}$, $R_{33}$, $R_{34}$, $R_{35}$, $R_{36}$, and $R_{37}$ wherein: $R_{31}$ is hydroxyl, halogen, cyano, carboxyl, trifluoromethyl, $C_{1-4}$ alkyl, $C_{1-4}$ alkoxy, $C_{1-4}$ alkoxycarbonyl, $C_{1-4}$ alkylcarbonyl, $C_{1-4}$ alkylcarbonyloxy, amino, mono- or di-$C_{1-4}$ alkylamino or $C_{1-4}$ alkylcarbonylamino; $R_{32}$ is hydrogen, hydroxyl, halogen, amino, trifluoromethyl, $C_{1-4}$ alkyl, or $C_{1-4}$ alkoxy; $R_{33}$ is hydrogen, halogen, amino, $C_{1-4}$ alkyl, or $C_{1-4}$ alkoxy; $R_{34}$ is hydroxyl, halogen, cyano, carboxyl, $C_{1-4}$ alkyl, $C_{1-4}$ alkoxy, $C_{1-4}$ alkoxycarbonyl, or amino; $R_{35}$ is hydrogen, halogen, amino, or $C_{1-4}$ alkyl; $R_{36}$ is hydrogen or halogen; and $R_{37}$ is hydrogen or halogen; to form a product comprised of the resultant 3,4-disubstituted benzamide.

48. A process as in claim 47 wherein the carbonylation is a palladium-catalyzed carbonylation in a liquid phase using carbon monoxide under superatmospheric pressure.

49. A process as in each of claim 47 or 48 wherein $R_1$ is a cyclopropylmethoxy group, $R_2$ is a bromine or iodine atom, and the carbonylation is effected using 4-amino-3,5-dichloropyridine so that said resultant 3,4-disubstituted benzamide is roflumilast.

50. An o-(cycloalkyl methoxy)-p-halophenol in which the cycloalkyl methoxy group is a $C_{3-7}$ cycloalkyl methoxy group, and in which the halo substituent is a chlorine, bromine or iodine atom.

51. An o-(cycloalkyl methoxy)p-halophenol according to claim 50 which is o-(cyclopropylmethoxy)-p-bromophenol.

* * * * *